United States Patent [19]
Gans et al.

[11] Patent Number: 5,648,389
[45] Date of Patent: Jul. 15, 1997

[54] COMPOSITIONS FOR THE TREATMENT OF DERMATOLOGICAL DISORDERS AND METHODS FOR THEIR USE

[75] Inventors: Eugene H. Gans; Jonah Shacknai, both of Phoenix, Ariz.

[73] Assignee: Medicis Pharmaceutical, Inc., Phoenix, Ariz.

[21] Appl. No.: 549,374

[22] Filed: Oct. 27, 1995

[51] Int. Cl.$^6$ ................................................. A01N 37/00
[52] U.S. Cl. ........................ 514/557; 424/59; 424/63; 424/70.11; 424/279.1; 424/283.1; 514/545; 514/772.3; 514/844; 514/847; 514/873; 514/941
[58] Field of Search ........................ 514/545, 557, 514/844, 847, 873, 472.3, 529, 941; 424/70.11, 59, 63, 274.1, 279, 283, 317, 319, 338

[56] References Cited

U.S. PATENT DOCUMENTS

| | | | |
|---|---|---|---|
| 4,363,815 | 12/1982 | Yu et al. | 424/274 |
| 4,895,727 | 1/1990 | Allen . | |
| 5,196,187 | 3/1993 | Nicoll et al. | 424/70 |
| 5,258,391 | 11/1993 | Van Scott et al. | 514/529 |
| 5,385,938 | 1/1995 | Yu et al. | 514/557 |

FOREIGN PATENT DOCUMENTS

| | | | |
|---|---|---|---|
| 224177 | 7/1984 | Czechoslovakia | A61K 31/60 |

OTHER PUBLICATIONS

*Goodman and Gilman's The Pharmacological Basis of Therapeutics*: Heavy Metals and Their Salts; 1980; p. 977.
Webster, M.D., Guy F.; *Journal of the American Academy of Dermatology*; "Inflammation in Acne Vulgaris"; 1955; pp. 33:247–253.
*Handbook of Nonprescription Drugs*; 9th Ed.; p. 798.

*Primary Examiner*—Terressa Mosley
*Attorney, Agent, or Firm*—William J. McNichol, Jr.

[57] ABSTRACT

The present invention provides compositions and methods for alleviation of both visible and non-visible, or pre-emergent, dermatological lesions associated with changes in normal keratinization, cutaneous infection, epidermal formation or pilosebaceous function, such as acne, psoriasis, seborrhea, ingrown hairs and pseudofolliculitis barbae, and hyperpigmented skin. The inventive compositions comprise a dermatologically absorbable topical antimicrobial, antibiotic, antibacterial or antifungal agent; a dermatologically absorbable alpha or beta hydroxy acid; and a dermatologically absorbable zinc compound in a suitable carrier.

18 Claims, No Drawings

COMPOSITIONS FOR THE TREATMENT OF DERMATOLOGICAL DISORDERS AND METHODS FOR THEIR USE

TECHNICAL FIELD OF THE INVENTION

This invention relates to compositions for the treatment of dermatological disorders and, in particular, to topical compositions for the treatment of dermatological conditions arising from changes in normal keratinization, epidermal formation or pilosebaceous function, such as acne, psoriasis, seborrhea, ingrown hairs and pseudofolliculitis barbae, and hyperpigmented skin.

BACKGROUND OF THE INVENTION

Ache, cutaneous infections, psoriasis and other disorders of the cutaneous and pilosebaceous unit or the process of keratogenesis are typically characterized by the presence of visible dermatological lesions, such as the raised closed comedones, the often colored open comedones, red or pustular-looking inflamed papules, pustules, nodules and cysts of acne or cutaneous infection; the readily visible ingrown hairs of pseudofolliculitis barbae; or the visible scales of seborrhea, ichthyosis and psoriasis. Clinical evaluation of potential treatments for such disorders is typically based on the effectiveness of the treatment in reducing the number and severity of these visible lesions.

Prior to the eruption of visible lesions on the surface of the skin, non-visible lesions, herein referred to as pre-emergent lesions, are generally present within the skin. While pre-emergent lesions are insufficiently visible to be graded in conventional clinical studies, their presence within the skin can be discerned by the tactile sense of feel and/or by pain and tension within the skin.

Pre-emergent lesions are caused by a pre-emergent process within the epidermis and dermis, or within and surrounding the pilosebaceous follicle, which is located within the skin's epidermis, dermis, or both. In acne, for example, this pre-emergent process usually begins within the pilosebaceous follicle. The pilosebaceous follicle is filled with sebum secreted into the follicle by the sebaceous gland, bacteria, (primarily corynebacterium acnes, or P. aches) and keratin cells which slough off the inner wall of the follicle. In the pre-emergent process, the follicular wall is attacked by inflammatory agents, in particular excess free fatty acids produced by the breakdown of triglycerides present in the sebum by lipolytic enzymes, or lipases, and chemotactic and inflammatory agents that are produced and induced from P. acnes. Research has shown that, compared to normal patients, acne patients have increased levels of sebum secretion and increased presence of P. acnes and its associated lipase activity, with a resulting increase in the level of free fatty acids and other associated inflammatory agents. These increases have been shown to be roughly proportional to the severity of the disorder.

In addition, acne patients often have abnormal follicular walls. In normal skin, the follicular wall is composed entirely of keratinized cells, formed by the process of keratinization. This keratinized cell wall forms a barrier between the sloughed keratin cells, and the sebaceous and bacterial components within the follicle and the aqueous tissue surrounding the follicle. In ache patients, faulty keratinization apparently allows structurally weaker sebum-containing cells to be inserted into the follicular wall, thereby making the wall more vulnerable to attack and rupture. Once the cell wall is breached, free fatty acids, sebaceous and inflammatory components, live and dead bacteria, sloughed cells from the follicular wall and other follicle contents are released into the aqueous tissue surrounding the follicle, where they establish an inflammatory process (Webster, G., Jnl. Am. Acad. Dermatol., 1955; 33:247–253).

The pre-emergent process described above can progress to the point where, though not visible on the surface, the inflammation and resulting internal lesions can be felt within the skin as a sensation or as pain, and may also be felt by touch on the surface of the skin as a bump.

While several studies have been published on the individual effects of agents such as benzoyl peroxide, alpha hydroxy acids and zinc agents on dermatological problems visible on the surface of the skin, such as non-inflamed comedones, inflamed papules and pustules, cutaneous infections, ingrown hairs, and keratotic scales (Handbook of Non-Prescription Drugs, American Pharmaceutical Association, 9th Ed. (1990) 798; Goodman and Gilman, Pharmacologic Basis of Therapeutics, MacMillan Publishing Co., 6th Ed. (1980), 977; Ruey, J. Y., Van Scott, E. J., U.S. Pat. No. 4,363,815), the inventors are unaware of any published reports of the efficacy of recognized acne drugs on pre-emergent lesions.

SUMMARY OF THE INVENTION

The present invention provides a method of treating dermatological disorders arising from changes in normal keratinization, epidermal formation or pilosebaceous function, such as acne, psoriasis, seborrhea, ingrown hairs and pseudofolliculitis barbae, and hyperpigmented skin, by the topical administration of a composition comprising a dermatologically absorbable topical antimicrobial, antibiotic, antibacterial or antifungal agent; a dermatologically absorbable alpha or beta hydroxy acid; and a dermatologically absorbable zinc compound in a dermatologically acceptable carrier. The compositions of the present invention are preferably applied to an affected area of a patient's skin on a daily basis, in the form of clear gels, opaque gels, lotions, suspensions, ointments, creams, powders and the like.

The dermatologically absorbable topical antimicrobial, antibiotic, antibacterial or antifungal agent is preferably selected from the group consisting of benzoyl peroxide, erythromycin, bacitracin, zinc bacitracin, polymyxin, neomycin, chloramphenicol, tetracycline, minocycline, clindamycin, doxycycline, undecylenic acid and salts thereof, propionic acid and salts thereof, caprylic acid and salts thereof, ciprofloxacin, cephalosporins, benzoic acid, ciclopirox olamine, clotrimazole, econazole nitrate, metronidazole, miconazol nitrate, ketaconazole, oxiconazole, tolnaftate and combinations thereof; and is most preferably benzoyl peroxide. The antimicrobial, antibiotic, antibacterial or antifungal agent may be present in an amount of between about 0.1% to about 30%, preferably between about 0.5% to about 10%. All percentages referred to herein are by weight.

The alpha or beta hydroxy acid agent is selected from the group consisting of free acids, salts, amides, amphoteric and polymeric forms of the following compounds: citric acid, glycolic acid, glucuronic acid, galacturonic acid, glucuronolactone, gluconolactone, alpha-hydroxybutyric acid, alpha-hydroxyisobutyric acid, lactic acid, malic acid, mandelic acid, mucic acid, pyruvic acid, methyl pyruvate, ethyl pyruvate, beta-phenyllactic acid, beta-phenylpyruvic acid, saccharic acid, tartaric acid, tartronic acid and beta-hydroxybutyric acid. In a preferred embodiment, the alpha or beta hydroxy acid is selected from the group consisting of glycolic acid, lactic acid, mandelic acid, citric acid, tartaric acid, malic acid, salicylic acid, and acetylsalicylic acid, and is most preferably glycolic acid or lactic acid. The alpha or beta hydroxy acid is present in an amount of between about 0.10% to about 70%, with a preferred concentration for brief application on the skin of between about 5% to about 70%, with a preferred concentration for daily use left on the skin after application of between about 0.5% to about 15%.

The zinc compound is selected from the group consisting of water soluble, poorly water soluble and water insoluble zinc salts, compounds and complexes, such as zinc acetate, zinc bacitracin, zinc bromide, zinc caprylate, zinc chloride, zinc citrate, zinc fluoride, zinc formate, zinc glycinate, zinc iodate, zinc lactate, zinc nitrate, zinc nitrite, zinc oleate, zinc oxalate, zinc oxide, zinc permanganate, zinc peroxide, zinc phenolsulfonate, zinc phosphate, zinc propionate, zinc pyrophosphate, zinc ricinoleate, zinc salicylate, zinc selenate, zinc silicate, zinc selenide, zinc sulfate, zinc stearate, zinc sulfide, zinc tannate, zinc tartrate, zinc valerate, zinc peptides, and zinc protein complexes. In a preferred embodiment of the present invention, the zinc compound is zinc lactate or zinc acetate, and is present in an amount of between about 0.001% to about 30%, most preferably between about 0.1% to about 10%.

Other therapeutic agents may be usefully added to the compositions of the present invention. Such agents include retinoids, such as trans retinoic acid, 13-cis retinoic acid and derivatives thereof; anti-androgens, such as spironolactone; metronidazole; and anti-inflammatory agents, such as hydrocortisone, betamethasone, clobetasole, fluocinonide, triamcinolone, desonide, and halcinonide. These therapeutic agents may be present in an amount of between about 0.001% to about 10.0%, preferably between about 0.01% to 5.0%.

The active ingredients of the present invention are combined in a dermatologically acceptable carrier composed of noncomedogenic and hypoallergenic agents, such as water, C12–15 alkyl benzoate, glycerin, cetyl stearyl alcohol, polyacrylamide, C13–14 isoparaffin, laureth-7, PEG-1000 stearate, steareth S-2, steareth S-20, sodium hydroxide, dimethisone, and disodium EDTA. Other carriers which may be usefully employed in the present invention are well known in the art.

DETAILED DESCRIPTION OF THE INVENTION

Example 1

Two formulations of the inventive composition, Formulas I and II, composed of the reagents shown in Table I were prepared using the following protocol.

Dissolve the disodium EDTA and the zinc lactate in 60° C. hot water (30% batch weight) and add the glycerin. Then add the polyacrylamide-C13–14 Isoparaffin-Laureth-7, and mix until uniform, to provide part A. Separately, dissolve the glycolic acid in an equal part of water and slowly add the sodium hydroxide. Add to part A and maintain at 60° C. Separately, heat steareth S-2 and S-20, glycerylmonostearate SE and cetylstearyl alcohol until fluid and uniform. Add this to part A with mixing until smooth. Add the dimethicone; start cooling to 40° C. Separately, disperse the benzoyl peroxide in the C12–15 alkyl benzoate and add to cooled part A. Finally, QS with water to 100% and homogenize if necessary.

TABLE I

| | % BY WEIGHT | |
|---|---|---|
| | FORMULA I | FORMULA II |
| benzoyl peroxide | 10.0 | 6.0 |
| C12–15 benzoate ester | 7.0 | 7.0 |
| glycerin | 6.0 | 6.0 |
| cetyl stearyl alcohol (C5–50, LIPO) | 4.0 | 4.0 |
| polyacrylamide, C12–14 isoparaffin and laureth-7 | 3.0 | 3.0 |
| glycolic acid | 4.0 | 2.0 |
| sodium hydroxide | 0.5 | 0.5 |
| steareth S-2 (LIPO) | 2.0 | 2.0 |
| glycerylmonostearate, SE | 2.0 | 2.0 |
| steareth S-20 (LIPO) | 1.5 | 1.5 |
| dimethicone 200 fluid (100 cps) (Dow Corning) | 1.0 | 1.0 |
| zinc lactate | 0.6 | 0.6 |
| disodium EDTA | 0.5 | 0.5 |
| water | to 100% | to 100% |

A third formulation of the inventive composition, specifically a gel that can be used as a cleanser or left on the skin for treatment, hereinafter referred to as Formula III, composed of the reagents shown in Table II was prepared as follows.

Petrolatum, sodium cocyl isethionate, potassium metaphosphate, titanium dioxide and zinc lactate were mixed and homogenized until smooth to form mixture I. Carbomer was dispersed in a portion of the glycerin, heated to 75° C. and added to mixture I, homogenizing if necessary until creamy, to form mixture II. Glycolic acid was dissolved in the remaining glycerin at 50° C. To this was added sodium hydroxide, previously dissolved in 5 parts of water. The resulting mixture was added to mixture II and then cooled to 45° C. to provide mixture III. Benzoyl peroxide was dispersed in C12–15 alkyl benzoate and added to mixture III. The resulting product was milled as needed.

TABLE II

| | % BY WEIGHT |
|---|---|
| glycerin, anhydrous | 50.0 |
| petrolatum | 15.0 |
| benzoyl peroxide | 10.0 |
| zinc lactate | 2.0 |
| sodium cocyl isethionate | 4.0 |
| alfa olefin sulfonate | 2.0 |
| potassium metaphosphate | 0.5 |
| C12–15 alkyl benzoate | 5.0 |
| glycolic acid | 0.25 |
| sodium hydroxide | 0.05 |
| carbomer | 0.7 |
| water | to 100% |

Example 2

Formula III of Example 1 was tested on two patients having persistent dermatological lesions; the lesions of both occurring mostly on the face and on the neck.

Both patients had suffered continually from inflamed papules, non-inflamed ingrown hairs, inflamed ingrown hairs and pre-emergent lesions. Prior to treatment with Formula III of the present invention, each patient had used a wide range of treatments, including topical benzoyl peroxide, topical erythromycin, topical erythromycin plus zinc, topical clindamycin, alpha hydroxy acid lotions, and topical erythromycin plus topical benzoyl peroxide. Each of these medications was used individually on a daily basis for at least two months. Each medication initially caused a reduction in the number and severity of dermatological lesions but this effect subsequently diminished. None of the medications was successful in substantially and consistently reducing the lesions, particularly the pre-emergent lesions.

Prior to treatment with Formula III of the present invention, the patients had a range of dermatological problems as shown in Table III.

TABLE III

|  | Patient 1 | Patient 2 |
|---|---|---|
| Emerging lesions | 3 to 6 | 4 to 8 |
| Redness | moderate patches | mild-moderate |
| Papules | 1 to 2 | 2 to 4 |
| Ingrown hairs | 1 to 3 | 2 to 5 |

Each patient applied Formula III topically twice daily to the effected area. The range of dermatological lesions present after treatment for one month and two months are shown in Tables IV and V, respectively.

TABLE IV

|  | Patient 1 | Patient 2 |
|---|---|---|
| Emerging lesions | 1 to 2 | 0 to 3 |
| Redness | mild-none | none |
| Papules | 0 to 1 | 0 to 2 |
| Ingrown hairs | 0 to 2 | 1 to 2 |

TABLE V

|  | Patient 1 | Patient 2 |
|---|---|---|
| Emerging lesions | 0 to 1 | 0 to 2 |
| Redness | none | none |
| Papules | 0 | 0 |
| Ingrown hairs | 0 to 1 | 0 |

These results demonstrate that the compositions of the present invention are effective in reducing the number and severity of both visible lesions, such as papules, and non-visible, pre-emergent lesions.

Although the present invention has been described in terms of specific embodiments, changes and modifications can be carried out without departing from the scope of the invention which is intended to be limited only by the scope of the appended claims.

We claim:

1. A composition for the treatment of acne, comprising:
   (a) a dermatologically absorbable topical antimicrobial, antibiotic, antibacterial or antifungal agent;
   (b) a dermatologically absorbable hydroxy acid selected from the group consisting of glycolic acid, salicylic acid and lactic acid;
   (c) a dermatologically absorbable, water soluble zinc compound; and
   (d) a dermatologically acceptable carrier.

2. The composition of claim 1, wherein the dermatologically absorbable topical antimicrobial, antibiotic, antibacterial or antifungal agent is selected from the group consisting of: benzoyl peroxide, erythromycin, bacitracin, zinc bacitracin, polymyxin, neomycin, chloramphenicol, tetracycline, minocycline, clindamycin, doxycycline, undecylenic acid and salts thereof, propionic acid and salts thereof, caprylic acid and salts thereof, ciprofloxacin, cephalosporins, benzoic acid, ciclopirox olamine, clotrimazole, econazole nitrate, metronidazole, miconazol nitrate, ketaconazole, oxiconazole, tolnaftate and combinations thereof.

3. The composition of claim 1, wherein the dermatologically absorbable topical antimicrobial, antibiotic, antibacterial or antifungal agent is benzoyl peroxide.

4. The composition of claim 1, wherein the dermatologically absorbable alpha or beta hydroxy acid is selected from the group consisting of: citric acid, glycolic acid, glucuronic acid, galacturonic acid, glucuronolactone, gluconolactone, alpha-hydroxybutyric acid, alpha-hydroxyisobutyric acid, lactic acid, malic acid, mandelic acid, mucic acid, pyruvic acid, methyl pyruvate, ethyl pyruvate, beta-phenyllactic acid, beta-phenylpyruvic acid, saccharic acid, tartaric acid, tartronic acid and beta-hydroxybutyric acid, and salts, amides, amphoteric and polymeric forms thereof.

5. The composition of claim 4, wherein the dermatologically absorbable alpha or beta hydroxy acid is selected from the group consisting of: glycolic acid, salicylic acid, and lactic acid.

6. The composition of claim 1, wherein the dermatologically absorbable zinc compound is selected from the group consisting of: zinc acetate, zinc bacitracin, zinc bromide, zinc caprylate, zinc chloride, zinc citrate, zinc fluoride, zinc formate, zinc glycinate, zinc iodate, zinc lactate, zinc nitrate, zinc nitrite, zinc oleate, zinc oxalate, zinc oxide, zinc permanganate, zinc peroxide, zinc phenolsulfonate, zinc phosphate, zinc propionate, zinc pyrophosphate, zinc ricinoleate, zinc salicylate, zinc selenate, zinc silicate, zinc selenide, zinc sulfate, zinc stearate, zinc sulfide, zinc tannate, zinc tartrate, zinc valerate, zinc peptides, and zinc protein complexes.

7. The composition of claim 3, wherein the dermatologically absorbable, water soluble zinc compound is selected from the group consisting of: zinc lactate and zinc acetate.

8. The composition of claim 7, wherein the benzoyl peroxide is present in an amount of between about 0.5% to about 10%.

9. The composition of claim 7, wherein the dermatologically absorbable hydroxy acid is present in an amount of between about 0.5% to about 15%.

10. The composition of claim 7, wherein the dermatologically absorbable, water soluble zinc compound is present in an amount of between about 0.1% to about 10%.

11. A method for the treatment of acne comprising administering a composition comprising:
   (a) a dermatologically absorbable topical antimicrobial, antibiotic, antibacterial or antifungal agent;
   (b) a dermatologically absorbable hydroxy acid selected from the group consisting of glycolic acid, salicylic acid and lactic acid; and
   (c) a dermatologically absorbable, water soluble zinc compound in a dermatologically acceptable carrier.

12. The method of claim 11, wherein the dermatologically absorbable topical antimicrobial, antibiotic, antibacterial or antifungal agent is benzoyl peroxide.

13. The method of claim 12, wherein the dermatologically absorbable zinc compound is selected from the group consisting of: zinc lactate and zinc acetate.

14. A method for the treatment of pre-emergent acne lesions, comprising administering a composition comprising:
   (a) a dermatologically absorbable topical antimicrobial, antibiotic, antibacterial or antifungal agent;
   (b) a dermatologically absorbable hydroxy acid selected from the group consisting of glycolic acid, salicylic acid and lactic acid;

(c) a dermatologically absorbable, water soluble zinc compound; and (d) a dermatologically acceptable carrier.

15. The method of claim 14, wherein the dermatologically absorbable topical antimicrobial, antibiotic, antibacterial or antifungal agent is benzoyl peroxide.

16. The method of claim 15, wherein the dermatologically absorbable zinc compound is selected from the group consisting of: zinc lactate and zinc acetate.

17. The method of claim 14, wherein:

a) the dermatologically absorbable topical antimicrobial, antibiotic, antibacterial or antifungal agent is benzoyl peroxide;

(b) the dermatologically absorbable alpha or beta hydroxy acid is selected from the group consisting of glycolic acid, salicylic acid, and lactic acid; and (c) the dermatologically absorbable zinc compound is selected from the group consisting of zinc lactate and zinc acetate.

18. The method of claim 14, wherein the dermatological disorder is selected from the group consisting of acne, psoriasis, seborrhea, ingrown hairs, pseudofolliculitis barbae, hyperpigmented skin, and cutaneous infection.

* * * * *